(12) United States Patent
Sekitani et al.

(10) Patent No.: US 12,121,356 B2
(45) Date of Patent: Oct. 22, 2024

(54) ELECTRODE SHEET

(71) Applicant: Osaka University, Osaka (JP)

(72) Inventors: Tsuyoshi Sekitani, Osaka (JP);
Shusuke Yoshimoto, Osaka (JP)

(73) Assignee: Osaka University, Osaka (JP)

( * ) Notice: Subject to any disclaimer, the term of this patent is extended or adjusted under 35 U.S.C. 154(b) by 1008 days.

(21) Appl. No.: 17/052,513

(22) PCT Filed: Mar. 26, 2019

(86) PCT No.: PCT/JP2019/012870
§ 371 (c)(1),
(2) Date: Nov. 2, 2020

(87) PCT Pub. No.: WO2019/211957
PCT Pub. Date: Nov. 7, 2019

(65) Prior Publication Data
US 2021/0236034 A1 Aug. 5, 2021

(30) Foreign Application Priority Data

May 2, 2018 (JP) ................................ 2018-088572

(51) Int. Cl.
*A61B 5/257* (2021.01)
*A61B 5/00* (2006.01)
(Continued)

(52) U.S. Cl.
CPC .............. *A61B 5/257* (2021.01); *A61B 5/282* (2021.01); *A61B 5/683* (2013.01)

(58) Field of Classification Search
CPC ......... A61B 5/257; A61B 5/282; A61B 5/683; A61B 5/259; A61B 5/28
See application file for complete search history.

(56) References Cited

U.S. PATENT DOCUMENTS 6,415,169 B1 * 7/2002 Kornrumpf ............ A61B 5/282
600/382
6,453,186 B1 * 9/2002 Lovejoy ................. A61B 5/282
600/386
(Continued)

FOREIGN PATENT DOCUMENTS

CN 105792735 A 7/2016
JP 6-2645 Y2 1/1994
(Continued)

OTHER PUBLICATIONS

International Search Report issued in application No. PCT/JP2019/012870, dated Jun. 10, 2019.
(Continued)

*Primary Examiner* — Adam Z Minchella
(74) *Attorney, Agent, or Firm* — Knobbe, Martens, Olson & Bear, LLP

(57) ABSTRACT

An electrode sheet is provided which can be flexibly adapted to the position where a signal is acquired. This electrode sheet 1, which is attached to a living body M and acquires a biological signal, is provided with a sheet-form biological signal acquisition unit 10 which is attached to a living body part where a biological signal is acquired, and a reference potential acquisition unit 20 which extends from the living body signal acquisition unit and which is attached to a living body part where a reference potential is acquired, wherein the reference potential acquisition unit 20 is provided with multiple electrodes 23 which are arranged at a prescribed interval along the direction of extension and each of which can attach to the living body part where the reference potential is acquired.

20 Claims, 7 Drawing Sheets

(51) Int. Cl.
*A61B 5/25* (2021.01)
*A61B 5/282* (2021.01)

(56) References Cited

U.S. PATENT DOCUMENTS

| | | | |
|---|---|---|---|
| 6,456,872 | B1 | 9/2002 | Faisandier |
| 2005/0251002 | A1* | 11/2005 | Istvan .................... A61B 5/274 |
| | | | 600/386 |
| 2007/0260133 | A1 | 11/2007 | Meyer |
| 2011/0190615 | A1* | 8/2011 | Phillips .................. A61B 5/282 |
| | | | 600/372 |
| 2013/0018251 | A1* | 1/2013 | Caprio .................... A61B 5/282 |
| | | | 29/831 |
| 2013/0281814 | A1 | 10/2013 | Tilt et al. |
| 2014/0206977 | A1 | 7/2014 | Bahney |
| 2014/0296681 | A1 | 10/2014 | Nakayama |
| 2015/0351689 | A1* | 12/2015 | Adams ................. A61B 5/6833 |
| | | | 600/300 |
| 2016/0128594 | A1 | 5/2016 | Amir |
| 2016/0262649 | A1 | 9/2016 | Hayes-Gill et al. |
| 2016/0310037 | A1 | 10/2016 | O'Neill |
| 2017/0164860 | A1* | 6/2017 | Hung ..................... A61B 5/259 |
| 2019/0029595 | A1 | 1/2019 | Sekitani |

FOREIGN PATENT DOCUMENTS

| | | |
|---|---|---|
| JP | 2007-301358 A | 11/2007 |
| JP | 2013-121489 A | 6/2013 |
| JP | 2014-8166 A | 1/2014 |
| JP | 2014-200270 A | 10/2014 |
| JP | 2016-153947 A | 8/2016 |
| JP | UP 2016-523110 A | 8/2016 |
| JP | 3207627 U | 11/2016 |
| JP | 2017-502777 A | 1/2017 |
| JP | 2017-136380 A | 8/2017 |
| JP | 2018-34486 A | 3/2018 |
| JP | 2018-042686 A | 3/2018 |
| WO | WO 2017/122379 A1 | 7/2017 |

OTHER PUBLICATIONS

Office Action issued in Chinese Patent Application No. CN201980029502.8, mailed on Jul. 1, 2023.

* cited by examiner

ELECTRODE SHEET

TECHNICAL FIELD

The present invention relates to an electrode sheet.

BACKGROUND ART

Conventionally, brain waves, a pulse and the like of a living body have been acquired as biological signals and the state of the living body has been analyzed. As a device capable of acquiring a biological signal, an electrode sheet that is pasted onto a living body and can acquire the biological signal, has been known.

As such an electrode sheet, an electrode sheet has been proposed that includes a stretchy resin sheet pastable onto a forehead and three electrodes provided thereon, thereby allowing brain waves to be measured (for example, see Patent Document 1). According to the proposed electrode sheet, by simply pasting the resin sheet onto a forehead, brain waves can be acquired, which can alleviate a burden on a patient during long-time measurement.

Patent Document 1: Japanese Unexamined Patent Application, Publication No. 2013-121489

SUMMARY OF THE INVENTION

Problems to be Solved by the Invention

In a case where a biological signal is acquired using the proposed electrode sheet, an electrode that acquires a reference potential (earth) serving as a reference is required. Preferably, the electrode that acquires the reference potential is pasted at a prescribed position, such as an earlobe or a hip, for example. That is, preferably, the electrode that acquires the reference potential is pasted at a prescribed position of a living body apart from the electrodes that acquire the biological signals.

Wiring is electrically connected to the electrode that acquires the reference potential and to electrodes that acquire the biological signals. Multiple wiring lines are connected to, for example, a communication device that can transmit the biological signals to the outside. The electrode that acquires the reference potential can be pasted at a prescribed position apart from the electrodes that acquire the biological signals, through a wiring line connected to the electrode that acquires the reference potential.

If the wiring line connected to the electrode that acquires the reference potential is too long, the wiring line is prone to noise, which sometimes hampers acquisition of the biological signals. If the wiring line connected to the electrode that acquires the reference potential is too short, the electrode that acquires the reference potential cannot be arranged at the prescribed position and the reference potential cannot be acquired in some cases. According to the body shape of the living body, the distance between the position at which the biological signal is acquired and the position (prescribed position) at which the reference potential is acquired varies. Accordingly, an electrode sheet is ideal that can flexibly accommodate the difference between the position at which the biological signal is acquired and the position (prescribed position) at which the reference potential is acquired. It is preferable to provide an electrode sheet that can flexibly accommodate the difference between the position at which the biological signal is acquired and the position at which the reference potential is acquired.

With a certain site at which a biological signal is acquired, the electrode sheet is required to be bent and pasted in conformity with a living body. It is preferable to provide an electrode sheet that can flexibly accommodate the size of the body and the difference in the body due to the age and be flexibly adapted to measurement at a site where the size varies in a short time, such as the abdomen of a pregnant woman. That is, it is preferable to provide an electrode sheet that can be flexibly adapted to a position at which the signal is acquired.

The present invention has an object to provide an electrode sheet that can be flexibly adapted to a position at which the signal is acquired.

Means for Solving the Problems

The present invention relates to an electrode sheet to be attached to a living body to acquire a biological signal, including: a sheet-shaped biological signal acquisition unit to be attached to a living body part at which the biological signal is acquired; and a reference potential acquisition unit to be attached to the living body part at which a reference potential is acquired, the reference potential acquisition unit acquiring the reference potential, the biological signal acquisition unit including: a sheet-shaped first flexible base material; a plurality of first electrodes that are arranged on one surface of the first flexible base material and are contactable with the living body part; and at least one separation part that is formed in the first flexible base material, is formed between prescribed ones of the first electrodes and includes one end arranged at an edge of the first flexible base material and another end arranged in a surface of the first flexible base material, the reference potential acquisition unit including a plurality of second electrodes that are arranged at a prescribed interval along an extending direction and are each attachable to the living body part at which the reference potential is acquired.

The present invention relates to an electrode sheet to be attached to a living body to acquire a biological signal, including a sheet-shaped biological signal acquisition unit to be attached to a living body part at which the biological signal is acquired, the biological signal acquisition unit including: a sheet-shaped first flexible base material; a plurality of first electrodes that are arranged on one surface of the first flexible base material and are contactable with the living body part; and at least one separation part that is formed in the first flexible base material, is formed between prescribed ones of the first electrodes and includes one end arranged at an edge of the first flexible base material and another end arranged in a surface of the first flexible base material.

Preferably, the separation part includes: a linear part that extends from one end to another end; and a hole part that has a circular shape in a plan view and is provided consecutively to the linear part at a position of the other end.

Preferably, the linear part is arranged so as not to intersect with another linear part.

Preferably, the biological signal acquisition unit further includes a board part that is overlaid on one surface of the first flexible base material and includes a notch part with a part overlapping the first flexible base material being cut out.

Preferably, the board part is divided into a plurality of areas and is peelable from the first flexible base material on an area-by-area basis.

Preferably, the notch part is arranged in the board part in an area-by-area basis.

Preferably, the biological signal acquisition unit further includes a sheet-shaped reinforcing member arranged to be overlaid on another surface of the first flexible base material along an edge of the other surface.

The present invention relates to an electrode sheet to be attached to a living body to acquire a biological signal, including: a sheet-shaped biological signal acquisition unit to be attached to a living body part at which the biological signal is acquired; and a reference potential acquisition unit that extends from the biological signal acquisition unit and is to be attached to a living body part at which a reference potential is acquired, the reference potential acquisition unit including a plurality of second electrodes that are arranged at a prescribed interval along an extending direction and are each attachable to the living body part at which the reference potential is acquired.

Preferably, the reference potential acquisition unit further includes: a sheet-shaped second flexible base material; and a second wiring line formed on the second flexible base material along the extending direction, and the second electrodes are each electrically connected to the second wiring line.

Preferably, a plurality of the reference potential acquisition units are provided so as to extend from the biological signal acquisition unit.

Preferably, a pair of the reference potential acquisition units are provided on opposite sides of the biological signal acquisition unit.

Preferably, the reference potential acquisition unit is provided in a folding back manner at a middle part in the extending direction.

Effects of the Invention

The present invention can provide an electrode sheet that can flexibly accommodate the difference between the position at which the biological signal is acquired and the position at which the reference potential is acquired.

DETAILED DESCRIPTION OF THE PREFERRED EMBODIMENT

An electrode sheet 1 according to each embodiment of the present invention is described with reference to FIGS. 1 to 8.

First Embodiment

Figure 1:
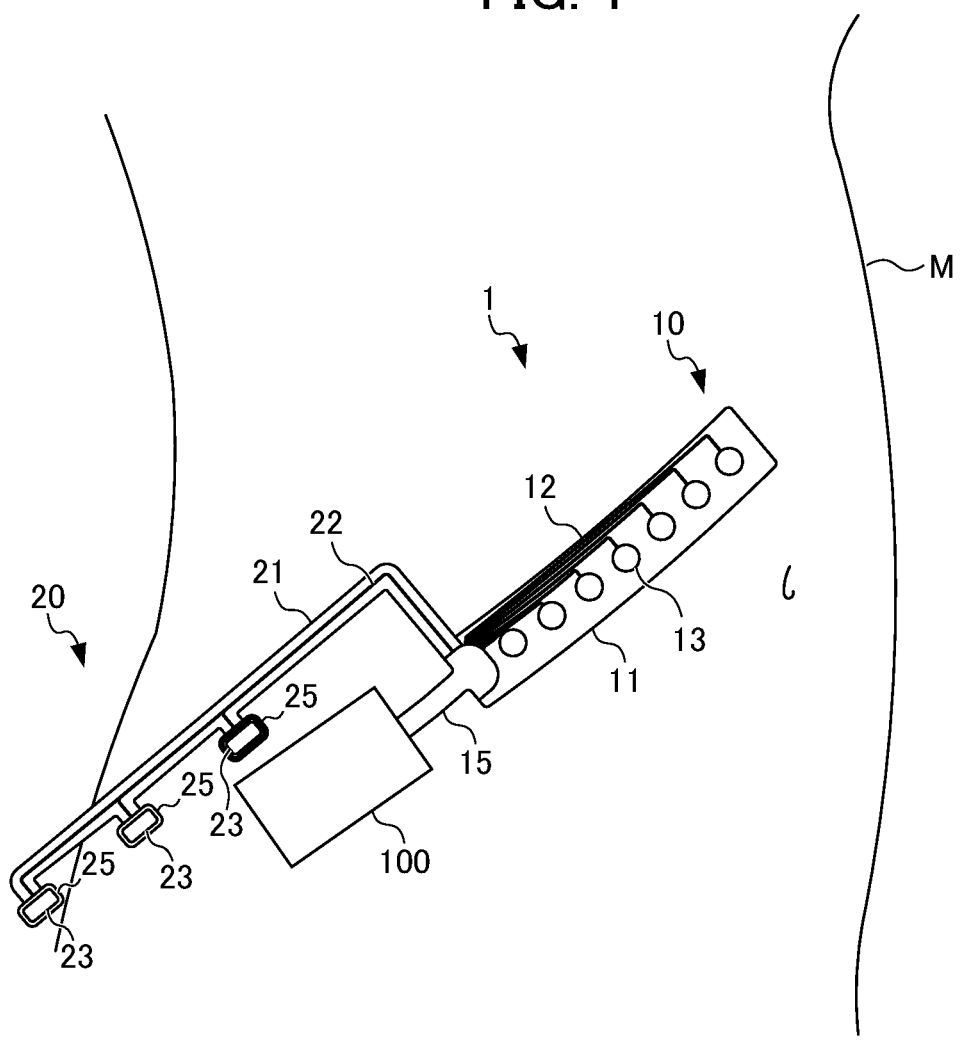
FIG. 1 is a schematic perspective view showing a state where an electrode sheet according to a first embodiment of the present invention is pasted onto a living body.

The electrode sheet 1 according to the first embodiment is attached to a living body M (human body) and is used to acquire a biological signal, such as a pulse, for example. Specifically, as shown in FIG. 1, the electrode sheet 1 according to the first embodiment is pasted onto the abdomen of a pregnant woman and is used to acquire the pulse of a fetus, as a biological signal. The electrode sheet 1 has stretching properties and flexibility, as a whole, and can be bent in conformity with the curved shape of the abdomen. Accordingly, the electrode sheet 1 can be in close contact with the abdomen and effectively acquire the pulse of the fetus.

A part of the electrode sheet 1 is pasted at a position of a hip of the pregnant woman. The part of the electrode sheet 1 acquires the potential at the position of the hip. That is, the part of the electrode sheet 1 acquires a reference potential with respect to the pulse of the fetus. Such an electrode sheet 1 includes a biological signal acquisition unit 10 and a reference potential acquisition unit 20.

Figure 2:
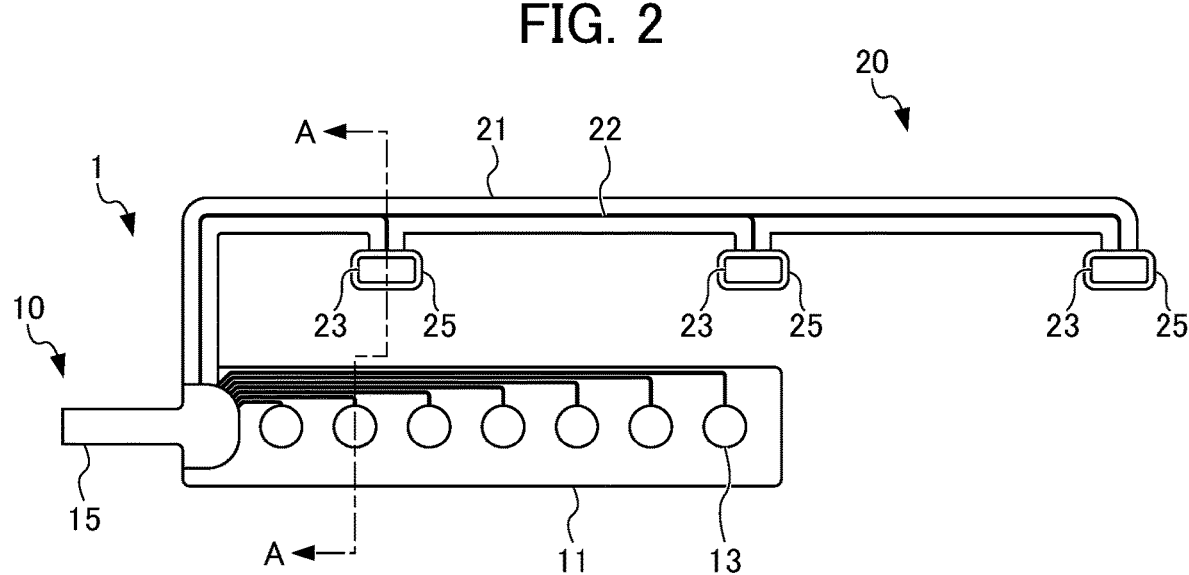
FIG. 2 is a plan view showing the electrode sheet of the first embodiment.
Figure 3:
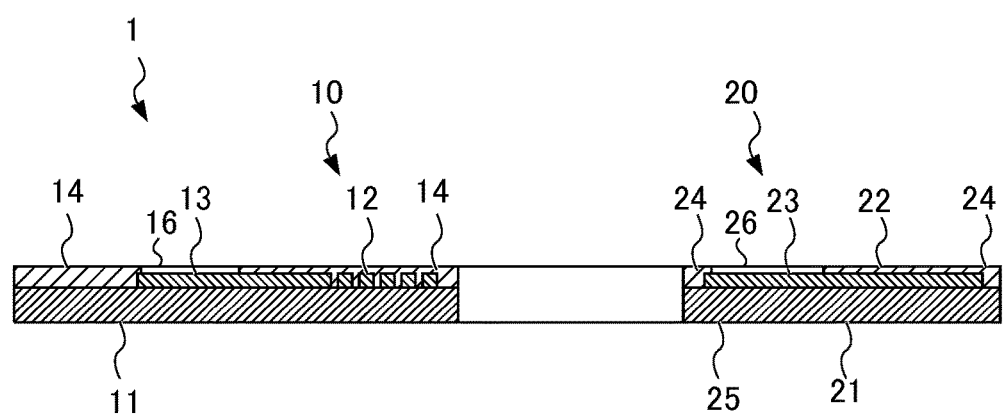
FIG. 3 is a sectional view taken along line A-A of FIG. 2.

The biological signal acquisition unit 10 is a sheet-shaped device attached to a living body part where a biological signal is acquired. As shown in FIGS. 1 to 3, the biological signal acquisition unit 10 includes a first flexible base material 11, first wiring lines 12, first electrodes 13, a first insulation layer 14 and a film base material 15.

The first flexible base material 11 is formed into a sheet shape with an elastomer material typified by a urethane series elastomer, for example. The first flexible base material 11 has a rectangular shape in plan view and has a shape with one side protruding outward from the surface. On the protruding side, the first flexible base material 11 is connectable to an external analysis device (not shown) or a wireless device 100 that wirelessly transmits a biological signal to the analysis device. Such a first flexible base material 11 has stretching properties stretching in an in-plane direction by an external force.

The first wiring lines 12 are made of a conductive material that contains a resin material (resin binder) and conductive particles dispersedly mixed therein. The first wiring lines 12 are formed to linearly cross over the first flexible base material 11. Specifically, the first wiring lines 12 are formed to cross over the surface of the first flexible base material 11 from the protruding side of the first flexible base material 11 to the opposite side. In this embodiment, multiple (seven) first wiring lines 12 are provided. The conductive material itself of the first wiring lines 12 have a significantly low Young's modulus (for example, 100 MPa or less; more preferably, 10 MPa or less) and exhibits a behavior of following expanding and contracting movements in the in-plane direction of the first flexible base material 11. The first wiring lines 12 can be formed by a printing method, for example.

The first electrodes 13 are made of a conductive material that contains a thermoplastic resin material (resin binder) and conductive particles dispersedly mixed therein. Such first electrodes 13 are formed to have circular shapes in a plan view on the first flexible base material 11 and are electrically connected to the first wiring lines 12. In this embodiment, the first electrodes 13 are arranged on a surface identical to a surface where the first wiring lines 12 are arranged, between the surfaces of the first flexible base material 11. The multiple first electrodes 13 are arranged along the direction where the first wiring lines 12 extend. Specifically, seven first electrodes 13 are consecutively arranged along the extending direction of the first wiring lines 12. The first electrodes 13 are arranged at positions preventing them from overlapping each other. Similar to the first wiring lines 12, the first electrodes 13 have a low Young's modulus (for example, 100 MPa or less; more preferably, 10 MPa or less) and have high following capability to the movement of the first flexible base material 11. The first electrodes 13 can be formed by a printing method, for example, accompanying formation of the first wiring lines 12.

The first insulation layer 14 is, for example, a stretchy sheet-shaped cover formed of an elastomer material and is overlaid on the first wiring lines 12. In this embodiment, the first insulation layer 14 is formed so as to be overlaid on the first flexible base material 11, exceeding the formation position of the first wiring lines 12. In particular, the first insulation layer 14 is formed to be overlaid on the rectangular area of the first flexible base material 11 and on a part of an area formed by the protruding side. Furthermore, the first insulation layer 14 has first through-holes 16 that have diameters smaller than the diameters of the first electrodes 135 and are disposed at positions overlaid on the respective first electrodes 135. Accordingly, the first through-holes 16 allow the first electrodes 13 to be exposed.

The film base material 15 is formed in conformity with the shape of the area formed by the protruding side of the first flexible base material 11 and is overlaid on the first wiring lines 12 and the surface of the first flexible base material 11. The film base material 15 is formed of a material having a higher in-plane stiffness than the first flexible base material 11. Accordingly, the first wiring lines 12 can be prevented from being broken, while the film base material 15 has an appropriate stiffness, which can improve the handling ability when the analysis device and the electrode sheet 1 (biological signal acquisition unit 10) are connected to each other.

According to the biological signal acquisition unit 10 described above, hydrogel or conductive adhesive (not shown) is applied on the exposed surface of the first insulation layer 14 and the biological signal acquisition unit 10 is attached at any measurement position (e.g., abdomen) of the living body M. Since the first flexible base material 11, the first wiring lines 12, the first electrodes 13 and the first insulation layer 14 have stretching properties, the biological signal acquisition unit 10 is in close contact with the living body M in a state of being curved in conformity with the shape of the living body M. Accordingly, the first electrodes 13 are in close contact with the living body M. Consequently, the first electrodes 13 can acquire biological signals at the positions in close contact. Meanwhile, the first wiring lines 12 are formed so as not to be in contact with the living body M by the first insulation layer 14. Accordingly, an unintended biological signal is prevented from being acquired through the first wiring lines 12. That is, noise is prevented from entering the biological signals acquired by the first electrodes 13. Furthermore, the film base material 15 having the high in-plane stiffness can protect the first wiring lines 12 arranged in an area formed by the protruding side of the first flexible base material 11. Consequently, the first wiring lines 12 can be protected from breaking.

The reference potential acquisition unit 20 extends from the biological signal acquisition unit 10. The reference potential acquisition unit 20 is attached to the living body part at which a reference potential is acquired. In this embodiment, the reference potential acquisition unit 20 extends in the in-plane direction of the biological signal acquisition unit 10 from one side along the extending direction of the first wiring lines 12 among the sides of the biological signal acquisition unit 10. In this embodiment, the reference potential acquisition unit 20 extends from a proximity of the film base material 15 of the biological signal acquisition unit 10. The reference potential acquisition unit 20 includes a second flexible base material 21, second wiring lines 22, second electrodes 23 and a second insulation layer 24.

The second flexible base material 21 is formed to have a sheet shape. This material is formed integrally with the first flexible base material 11. Specifically, the second flexible base material 21 is formed to have the same material and the same thickness as the first flexible base material 11. The second flexible base material 21 is formed to have a linear shape. The second flexible base material 21 includes multiple protruding pieces 25 that protrude in the in-plane direction at prescribed intervals along the extending direction. In this embodiment, each of the protruding pieces 25 protrudes from one side in a direction intersecting with the extending direction. The second flexible base material 21 is provided in a manner folding back at a middle part in the extending direction.

The second wiring lines 22 are formed of the same material as that of the first wiring lines 12. The second wiring lines 22 are formed on the second flexible base material 21 along the extending direction of the second flexible base material 21. The second wiring lines 22 is arranged from the protruding side of the first flexible base material 11, through the proximal end portion of the second flexible base material 21 in the extending direction, to the distal end of the second flexible base material 21.

The second electrodes 23 are formed of the same material as that of the first electrodes 13. The second electrodes 23 are arranged at prescribed intervals along the extending direction of the second flexible base material 21. In this embodiment, the second electrodes 23 are disposed on the respective protruding pieces 25 of the second flexible base material 21. Each of the second electrodes 23 is formed to be rectangular in a plan view. Each of the second electrodes 23 is configured so as to be attachable to the living body part at which the reference potential is acquired. In this embodiment, each of the second electrodes 23 is configured to be attachable to a position of the hip of the living body M. The second electrodes 23 can be formed by a printing method, for example, accompanying formation of the first electrodes 13, the first wiring lines 12 and the second wiring lines 22.

The second insulation layer 24 is a stretchy sheet-shaped cover formed of the same material as the first insulation layer 14 and is arranged overlaid on the second wiring lines 22. In this embodiment, the second insulation layer 24 is formed so as to overlaid on the second flexible base material 21, exceeding the formation position of the second wiring lines 22. In particular, the second insulation layer 24 is formed to be overlaid on the linear area of the second flexible base material 21 and parts of the protruding pieces 25. Furthermore, the second insulation layer 24 has rectangular second through-holes 26 which are smaller than the second electrodes 23 and are disposed at positions overlaid on the respective second electrodes 23. Accordingly, the second through-holes 26 allow the second electrodes 23 to be exposed.

According to the reference potential acquisition unit 20 as described above, hydrogel or conductive adhesive (not shown) is arranged on the surface of the second insulation layer 24 arranged at the positions of the protruding pieces 25, by application, printing or another method. Accordingly, the second electrodes 23 of the reference potential acquisition unit 20 can be pasted at a position of the hip of the living body M. Since the second flexible base material 21, the second wiring lines 22 and the second insulation layer 24 have stretching properties, the reference potential acquisition unit 20 can be expanded in conformity with the position (e.g., the position of the hip) at which the reference potential is acquired. The second electrodes 23 are selectively pasted on the living body M in conformity with the position at which the reference potential is acquired. Since the second electrodes 23 have stretching properties, the selected second electrode 23 is in close contact with the living body M in a state of being curved in conformity with the shape of the living body M. Accordingly, the second electrodes 23 are in close contact with the living body M. Consequently, the second electrodes 23 can acquire the reference potential at the position in close contact. Meanwhile, the second wiring lines 22 are formed so as not to be in contact with the living body M, by the second insulation layer 24. Accordingly, an unintended biological signal is prevented from being acquired through the second wiring lines 22. That is, noise is prevented from entering the biological signals acquired by the second electrodes 23.

The electrode sheet 1 as described above are used as follows. First, the biological signal acquisition unit 10 is pasted at a position of the abdomen of the living body M. Specifically, the biological signal acquisition unit 10 is pasted on the abdomen in a state where the exposed surfaces of the first electrodes 13 face the abdomen. At this time, as shown in FIG. 1, the biological signal acquisition unit 10 is pasted onto the abdomen such that the first electrodes 13 are arranged along a direction from the left shoulder to the right hip of the living body M, in a state of being aligned with the position of a fetus. Accordingly, the biological signal acquisition unit 10 can acquire the pulse of the fetus as a biological signal.

Next, the reference potential acquisition unit 20 is extended to the position of the right hip. The second electrode 23 closest to the position of the hip among the second electrodes 23 is selected as an electrode that acquires the reference potential. The selected second electrode 23 is pasted on the abdomen in a state where the exposed surface faces the right hip. In FIG. 1, the second electrode 23 closest to the biological signal acquisition unit 10 among the second electrodes 23 is pasted onto the right hip. Accordingly, the reference potential acquisition unit 20 can acquire the reference potential of the living body M. As described above, the electrode sheet 1 can acquire the pulse of the fetus as the biological signal and acquire the reference potential of the living body M.

As the fetus grows, the abdomen becomes larger. Accordingly, the distance between the position of the abdomen and the position of the right hip increases. As shown in FIG. 3, the second electrode 23 having the second longest distance from the biological signal acquisition unit 10 among the second electrodes 23 is selected as an electrode that acquires the reference potential. The selected second electrode 23 is pasted onto the right hip. Accordingly, even when the fetus grows, the reference potential acquisition unit 20 can acquire the reference potential of the living body M.

Figure 4:
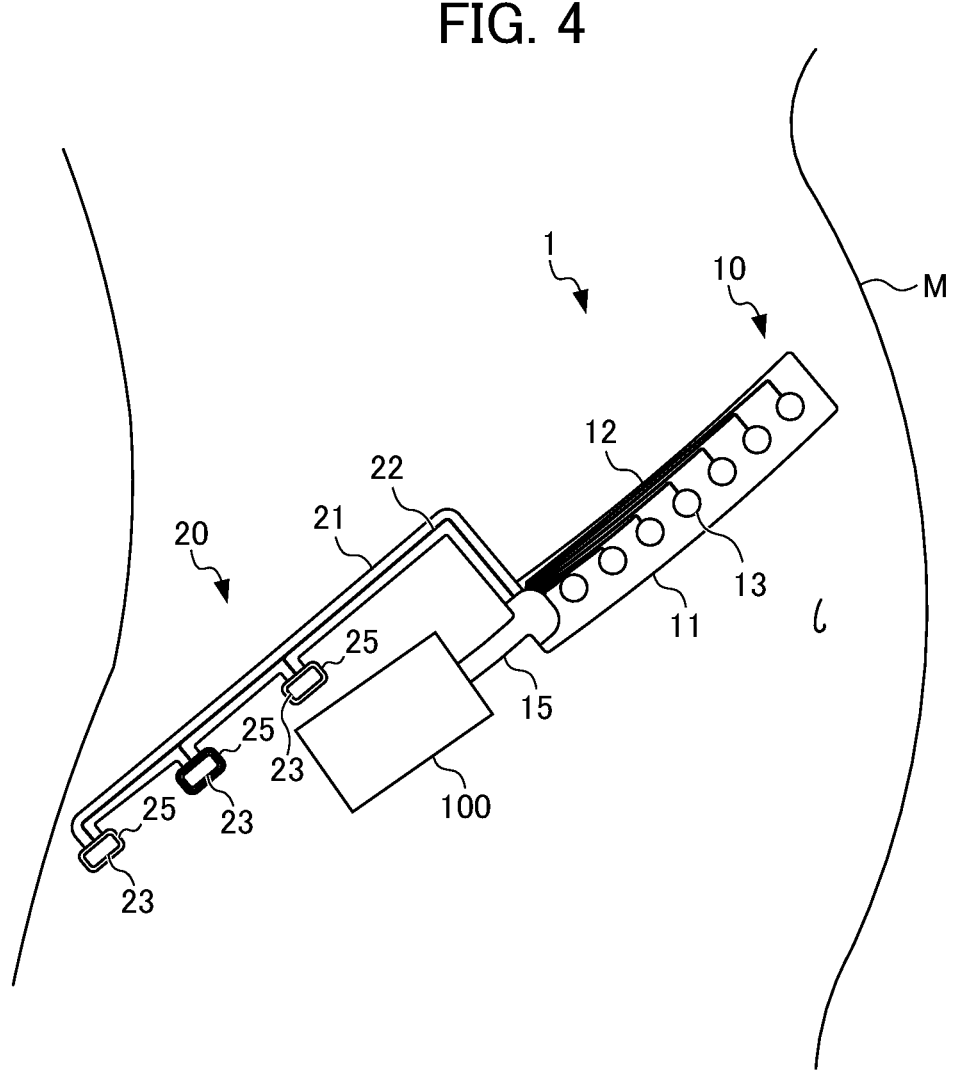
FIG. 4 is a schematic perspective view showing a state where a reference potential acquisition electrode of the electrode sheet of the first embodiment is changed.
Figure 5:
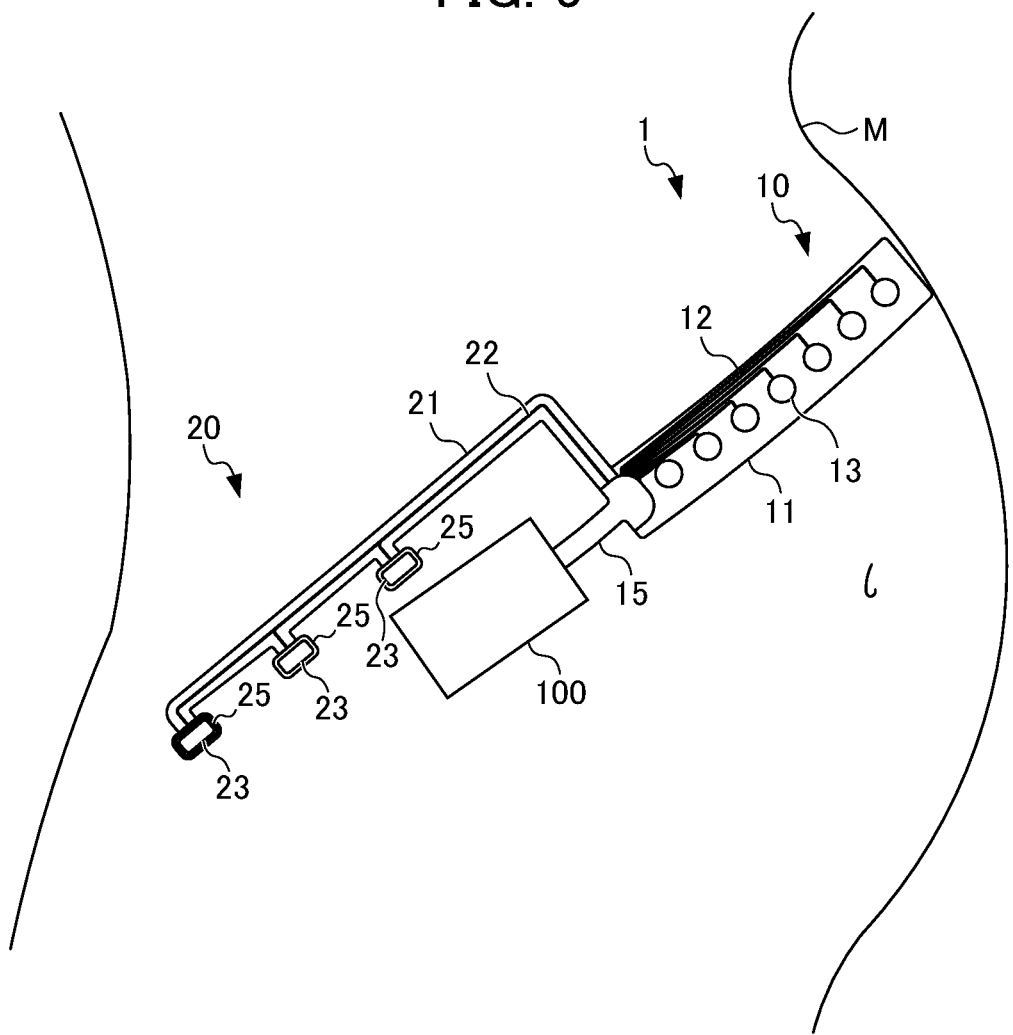
FIG. 5 is a schematic perspective view showing a state where the reference potential acquisition electrode of the electrode sheet of the first embodiment is further changed.

As the fetus further grows, the abdomen further becomes larger. Accordingly, the distance between the position of the abdomen and the position of the right hip further increases. As shown in FIG. 4, the second electrode 23 having the longest distance from the biological signal acquisition unit 10 among the second electrodes 23 is selected as an electrode that acquires the reference potential. The selected second electrode 23 is pasted onto the right hip. Accordingly, even when the fetus grows, the reference potential acquisition unit 20 can acquire the reference potential of the living body M.

The electrode sheet 1 in the first embodiment having been described above exerts the following advantageous effects.
(1) The electrode sheet 1 is the electrode sheet 1 to be attached to the living body M to acquire the biological signal, including: a sheet-shaped biological signal acquisition unit 10 to be attached to the living body part at which the biological signal is acquired; and a reference potential acquisition unit 20 that extends from the biological signal acquisition unit 10 and is attached to the living body part at which the reference potential is acquired. The reference potential acquisition unit 20 includes a plurality of second electrodes 23 that are arranged at a prescribed interval along the extending direction and are each attachable to the living body part at which the reference potential is acquired. Accordingly, the electrode sheet 1 can be provided that can flexibly accommodate the difference between the position at which the biological signal is acquired and the position at which the reference potential is acquired. Consequently, irrespective of the change of the living body M, the optimal reference potential can be acquired.

(2) The reference potential acquisition unit 20 further includes: the sheet-shaped second flexible base material 21; a wiring line formed on the second flexible base material 21 along the extending direction. The second electrodes 23 are each electrically connected to the second wiring lines 22. Accordingly, the reference potential acquisition unit 20 is allowed to have stretching properties. Consequently, the electrode sheet 1 can be provided that can more flexibly accommodate the difference between the position at which the biological signal is acquired and the position at which the reference potential is acquired.

(3) The reference potential acquisition unit 20 is provided in a manner folding back at the middle part in the extending direction. Accordingly, the electrode sheet 1 can be configured to be compact.

Second Embodiment

Figure 6:
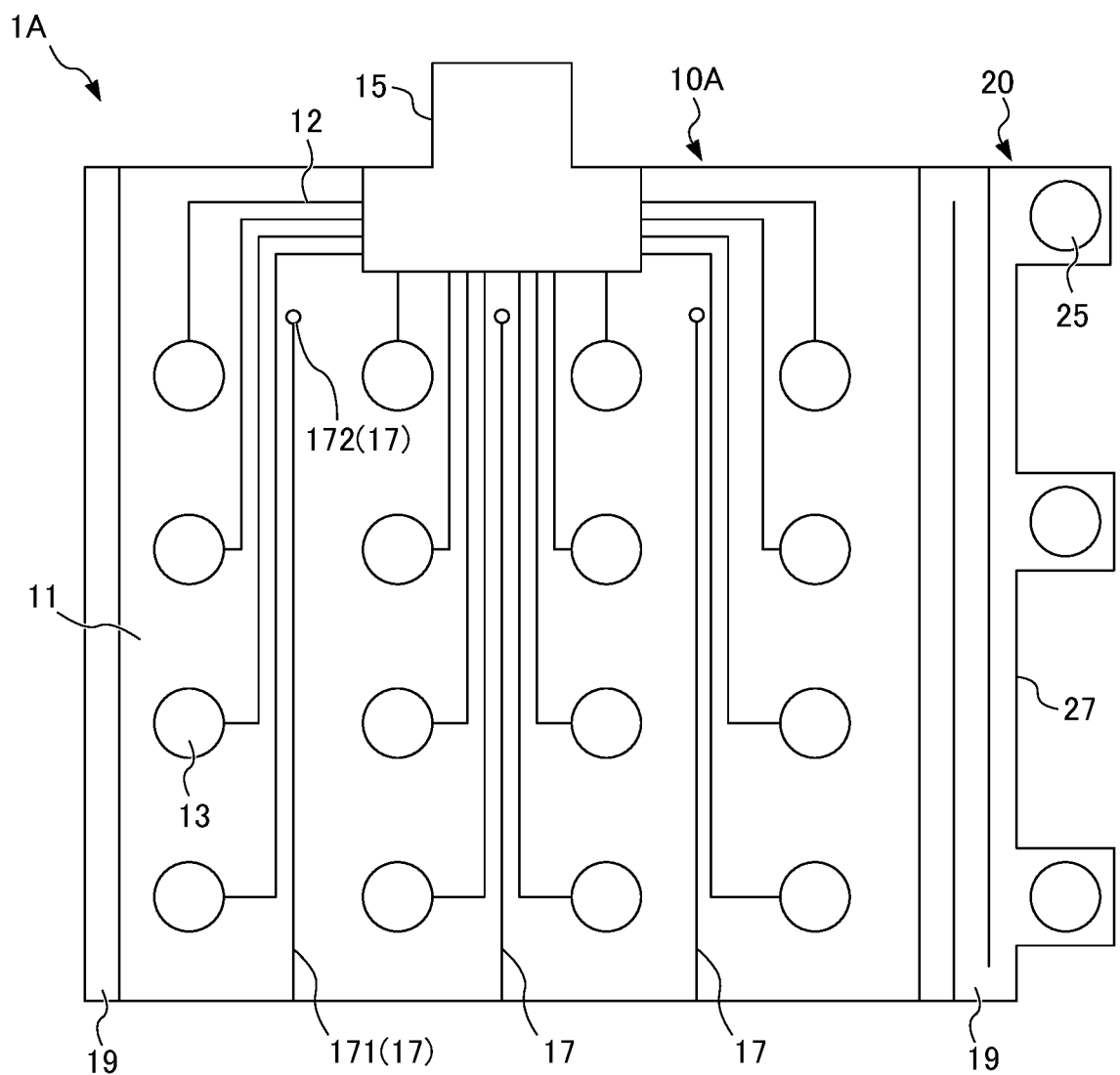
FIG. 6 is a plan view showing one surface of an electrode sheet of a second embodiment of the present invention.
Figure 7:
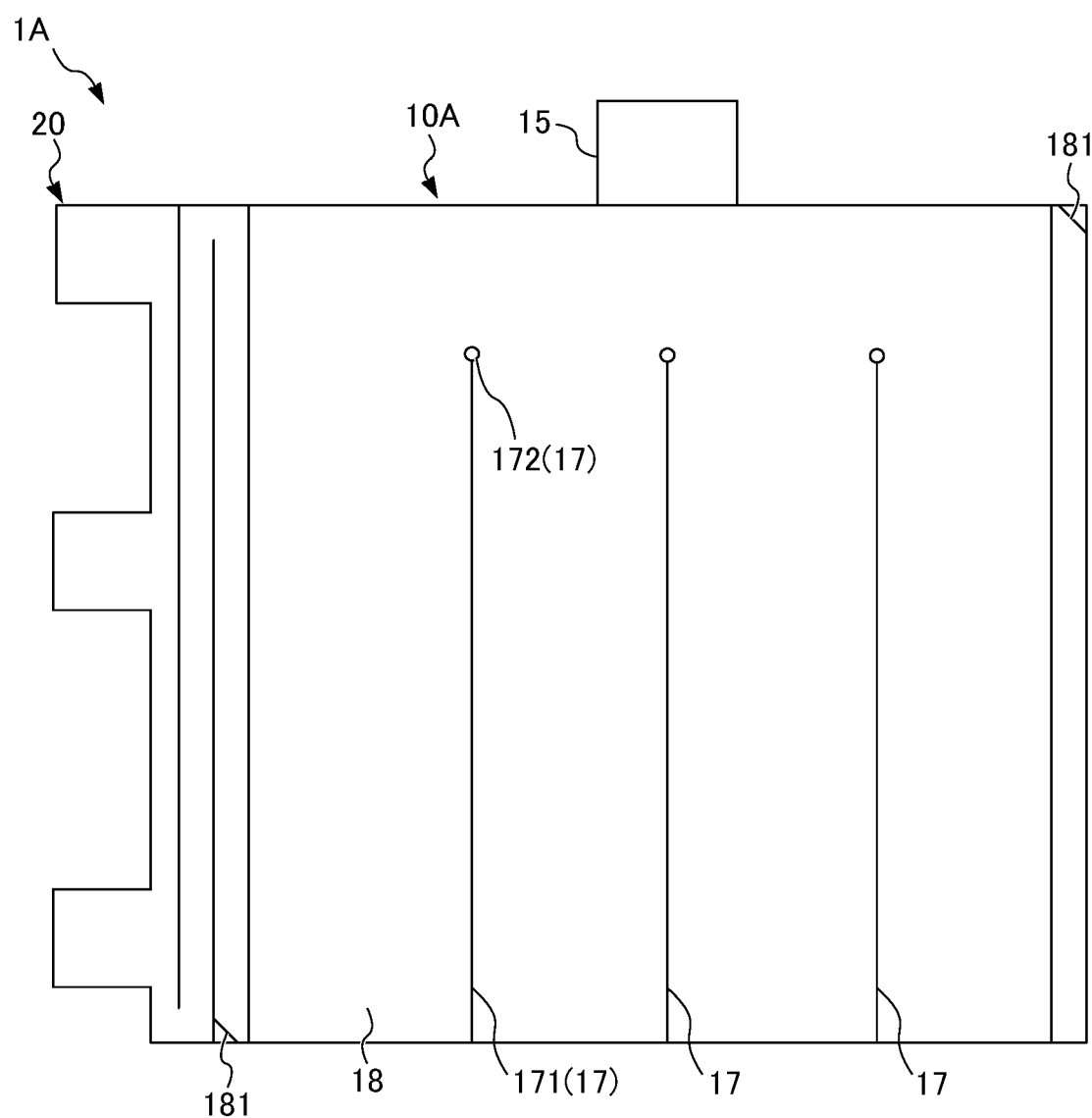
FIG. 7 is a plan view showing the other surface of the electrode sheet of the second embodiment.
Figure 8:
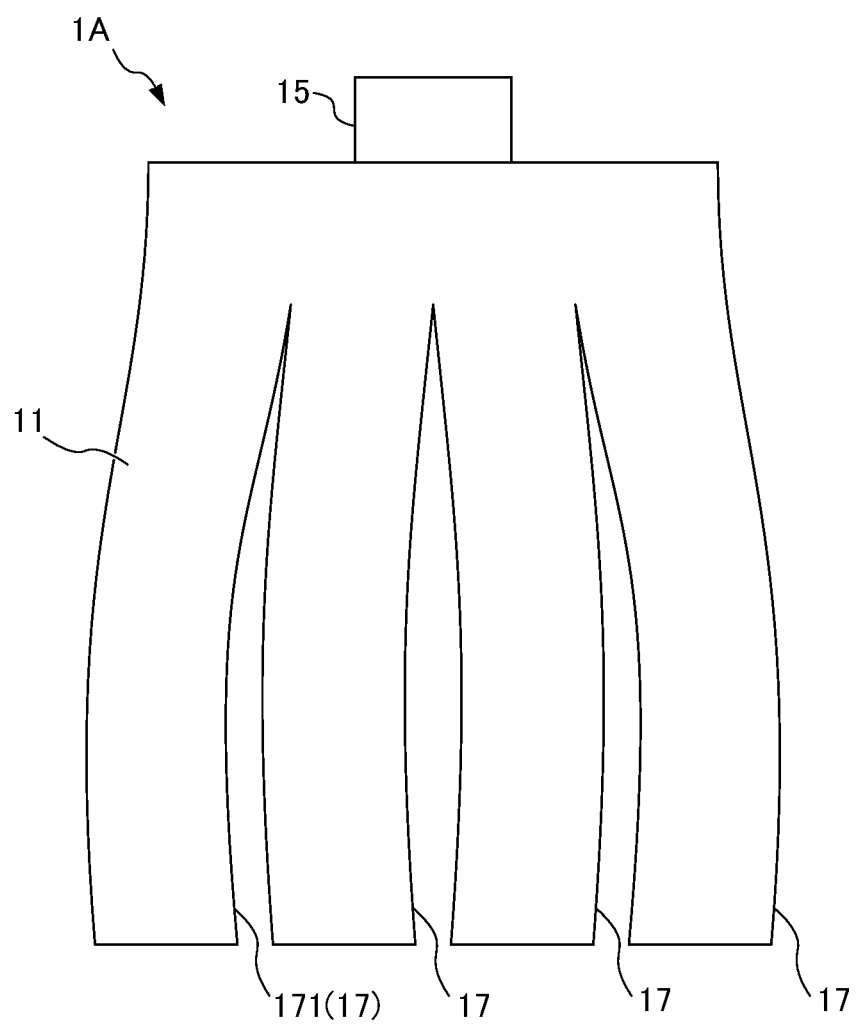
FIG. 8 is a schematic diagram showing a state where the electrode sheet of the second embodiment is spread.

Next, an electrode sheet 1A according to a second embodiment of the present invention is described with reference to FIGS. 6 to 8. As shown in FIGS. 6 and 7, the electrode sheet 1A according to the second embodiment is different from the first embodiment in the configuration of a biological signal acquisition unit 10A. Specifically, the biological signal acquisition unit 10A is different from the first embodiment in that this unit includes at least one separation part 17, a board part 18 and a reinforcing member 19. Note that the first electrodes 13 in this embodiment are arranged in a matrix manner. That is, the plurality of first electrodes 13 in this embodiment are arranged in the row direction and the column direction.

The separation part 17 is formed in the first flexible base material 11 and is formed between prescribed first electrodes 13. One end of the separation part 17 is arranged on an edge of the first flexible base material 11 and the other end is arranged in the surface of the first flexible base material 11. The separation part 17 is configured, for example, by separating the first flexible base material 11 into multiple strips as shown in FIG. 8. The separation part 17 includes a linear part 171 and a hole part 172.

The linear part 171 extends from one end to the other end. The linear part 171 is, for example, an incision. The linear part 171 is arranged so as not to intersect with the other linear parts 171. That is, the linear part 171 is arranged so as not to fragment (disjoint) the first flexible base material 11 into multiple areas. In this embodiment, three linear parts 171 are formed. The three linear parts 171 are arranged as slits that extend from one edge of the first flexible base material 11 in parallel or substantially parallel with each other. That is, the three linear parts 171 are formed to separate the first electrodes 13 in the row direction of the first flexible base material 11.

The hole parts 172 are arranged through the first flexible member. The hole part 172 has a circular shape in a plan view and is provided consecutively to the linear part 171 at a position of the other end. In this embodiment, the hole part 172 is arranged so as to communicate with the linear part 171 at the position of the other end of the linear part 171. Accordingly, the hole part 172 is arranged such that a part of the inner circumferential surface is divided by the linear part 171 in the thickness direction of the first flexible base material 11.

The board part 18 is, for example, release paper. The board part 18 is overlaid on the one surface of the first flexible base material 11. Specifically, the board part 18 is arranged adjacent to the first insulation layer 14, for example. In this embodiment, the board part 18 is formed to have the same or substantially same size and shape as the first flexible base material 11 has. As shown in FIG. 7, a notch part 181 is formed at the board part 18.

The notch part 181 is formed by cutting off a part of the board part 18. Specifically, the notch part 181 is formed by cutting off the part of the board part 18 that is to overlap the first flexible base material 11. The notch part 181 is formed by cutting out a corner of the first flexible base material 11, for example. The notch part 181 is arranged, for example, at a position overlapping a reinforcing member 19 described later.

The reinforcing member 19 has a sheet shape and is arranged overlaid on another surface of the first flexible base material 11 along an edge of the other surface. The reinforcing member 19 is formed of, for example, a material having a higher in-plane stiffness than the first flexible base material 11 has. In this embodiment, the reinforcing members 19 are respectively arranged along a pair of edges adjacent to the edge where the one end of the separation part 17 is arranged among the edges of the first flexible base material 11.

The electrode sheet 1A described above are used as follows. The board part 18 is peeled off the first flexible base material 11 (first insulation layer 14). For example, the first flexible base material 11 is bent together with the reinforcing member 19 at a position where the notch part 181 is formed, thereby allowing the board part 18 to be peeled off the first flexible base material 11 from a starting point that is the position of the notch part 181. The board part 18 is peeled off the first flexible base material 11, thereby allowing the biological signal acquisition unit 10A to be pastable onto the living body.

When the biological signal acquisition unit 10A is attached to the living body, the biological signal acquisition unit 10A is curved in conformity with the curve of the living body. At this time, the separation parts 17 divide the first flexible base material 11 into areas in conformity with the curve of the first flexible base material 11. That is, the separation parts 17 separates the areas of the first flexible base material 11 in conformity with the curve of the first flexible base material 11. For example, the separation part 17 allows the first flexible base material 11 to be separated from the other end to the one end, thereby enabling the first electrodes 13 to be arranged at positions where the biological signal is acquired.

For example, in a case where the biological signal acquisition unit 10A is pasted onto the abdomen of a pregnant woman, the size of the abdomen is different among early pregnancy, mid pregnancy and late pregnancy. The size of the abdomen is different also depending on the individual difference of the size of the fetus. The separation part 17 allows the first flexible base material 11 to be separated in conformity with the degree of the curve of the abdomen of the pregnant woman, thereby enabling the first electrodes 13 to be arranged at positions where the biological signal is acquired. The separation part 17 allows the first flexible base material 11 to be separated in conformity with the curve of the signal acquisition position (e.g., a shoulder, a chin, an arm, a leg, etc.) on the living body, thereby enabling the first electrodes 13 to be arranged at positions where the biological signal is acquired.

The electrode sheet 1A in the second embodiment having been described above exerts the following advantageous effects. (4) An electrode sheet 1A to be attached to a living body to acquire a biological signal, includes: a sheet-shaped biological signal acquisition unit 10A to be attached to a living body part at which the biological signal is acquired; and a reference potential acquisition unit to be attached to the living body part at which the reference potential is acquired, the reference potential acquisition unit acquiring the reference potential, the biological signal acquisition unit 10A including: a sheet-shaped first flexible base material 11; a plurality of first electrodes 13 that are arranged on one surface of the first flexible base material 11 and are contactable with the living body part; and at least one separation part 17 that is formed in the first flexible base material 11, is formed between prescribed ones of the first electrodes 13 and includes one end arranged at an edge of the first flexible base material 11 and another end arranged in a surface of the first flexible base material 11, the reference potential acquisition unit including a plurality of second electrodes that are arranged at a prescribed interval along an extending direction and are each attachable to the living body part at which the reference potential is acquired. Accordingly, the first flexible base material 11 can be separated in conformity with the curve of the living body. Consequently, the flexibility of the arrangement of the first electrodes 13 on the living body can be improved. Consequently, the general versatility of the electrode sheet 1A can be improved. For example, irrespective of the month of pregnancy, the biological signal can be acquired by one type of electrode sheet 1A. Without limitation to the abdomen, at any of various sites, such as a shoulder and a chin, the biological signal can be acquired. The electrode sheet 1A in the second embodiment includes multiple second electrodes. Accordingly, the optimal reference potential can be acquired.

(5) The separation part 17 includes: a linear part 171 that extends from one end to another end; and a hole part 172 that has a circular shape in a plan view and is provided consecutively to the linear part 171 at a position of the other end. Accordingly, the stress applied on the other end of the linear part 171 can be dispersed by the hole part 172. Consequently, the first flexible base material 11 can be prevented from being separated beyond the hole parts 172.

(6) The linear part 171 is arranged so as not to intersect with the other linear parts 171. Accordingly, the flexibility of arrangement of the first electrodes 13 can be improved without fragmenting the first flexible base material 11.

(7) The biological signal acquisition unit 10A further includes a board part 18 that is overlaid on one surface of the first flexible base material 11 and includes a notch part 181 with a part overlapping the first flexible base material 11 being cut out. Accordingly, the first flexible base material 11 can be handled without expansion and contraction. Consequently, the usability of the electrode sheet 1A can be improved. Furthermore, the board part 18 can be easily taken off the first flexible base material 11 by the notch parts 181. Accordingly, the usability of the electrode sheet 1A can be further improved.

(8) The biological signal acquisition unit 10A further includes a sheet-shaped reinforcing member 19 arranged to be overlaid on another surface of the first flexible base material 11 along an edge of the other surface. The board part 18 can thus be easily taken off the first flexible base material 11. Accordingly, the usability of the electrode sheet 1A can be further improved.

The preferable embodiments of the electrode sheets of the present invention have thus been described. However, the present invention is not limited to the aforementioned embodiments and can be appropriately changed. For example, in each of the aforementioned embodiments, the description has been made with one reference potential acquisition unit 20. However, the number is not limited thereto. Multiple reference potential acquisition units 20 may be provided so as to extend from the biological signal acquisition unit 10. For example, a pair of the reference potential acquisition units 20 may be provided on opposite sides of the biological signal acquisition unit 10. Specifically, the pair of the reference potential acquisition units 20 may be provided in the in-plane direction on opposite sides of the biological signal acquisition unit 10. Accordingly, the reference potential acquisition unit 20 reaching a position at which a more optimal reference potential can be acquired may be used to acquire the reference potential.

In the aforementioned embodiments, the examples where the electrode sheets 1 and 1A acquire the fetal movement of the fetus as the biological signal have been described. However, there is no limitation thereto. For example, the electrode sheets 1 and 1A may be attached to the chest of the living body M and acquire the pulse of the living body M. The electrode sheets 1 and 1A may be wound around a wrist and acquire the pulse of the living body M. In any of the cases, the reference potential acquisition unit 20 can be pasted on a reference potential acquisition position varying according to the difference of the body shape. Consequently, the electrode sheets 1 and 1A can flexibly acquire the reference potential without being affected by the difference in body shape.

In each of the embodiments described above, the electrode sheets 1 and 1A are configured to allow the first electrodes 13 to be pasted at the positions from the right shoulder to the right hip of the living body M. However, there is no limitation thereto. The electrode sheets 1 and 1A may be attached to the living body M in any manner as long as the fetal movement of the fetus can be acquired as a biological signal. The biological signal acquisition unit 10 may be attached to the living body M allowing the first electrodes 13 to be arranged from the right shoulder to the left hip of the living body M.

In each of the embodiments described above, the description has been made with the example where the number of first electrodes 13 is seven. The number is not limited thereto. Furthermore, the description has been made with the example where the number of second electrodes 23 is three. The number is not limited thereto. The number of first electrodes 13 is not limited as long as the number is plural. Furthermore, the number of second electrodes 23 is not limited as long as the number is plural.

In the aforementioned second embodiment, the description has been made using the example where the linear parts 171 are formed by preliminarily cutting the first flexible base material 11. However, there is no limitation thereto. The linear parts 171 may be formed such that the parts can be cut off. The linear parts 171 may be formed of perforations, for example. The linear parts 171 may be depressions formed along cut-off positions. The linear parts 171 are not limited to straight lines. The parts may be curved lines, bent lines or V-shapes that flare toward one end.

In the aforementioned second embodiment, the board part 18 may be divided into multiple areas and may be peelable from the first flexible base material 11 on an area-by-area basis. The notch parts 181 may be arranged in the respective areas of the board part 18. Accordingly, the usability of the electrode sheet 1A can be further improved in comparison with a case where the biological signal acquisition unit 10A is pasted onto the living body in a state with the completely peeled board part 18. For example, a partial area of the board part 18 may be peeled off, the first flexible base material 11 at the peeled position may be pasted on the living body and subsequently the board part 18 at another area may be peeled off.

EXPLANATION OF REFERENCE NUMERALS 1, 1A Electrode sheet
10, 10A Biological signal acquisition unit
17 Separation part
18 Board part
19 Reinforcing member
20 Reference potential acquisition unit
21 Second flexible base material
22 Second wiring line
23 Second electrode
171 Linear part
172 Hole part
181 Notch part
M Living body

What is claimed is:

1. An electrode sheet for acquiring a biological signal, comprising:
a biological signal acquisition sheet configured to be attached to a first living body part at which the biological signal is acquired; and
a reference potential acquisition sheet configured to be attached to a second living body part at which a reference potential is acquired, the reference potential acquisition sheet acquiring the reference potential,
the biological signal acquisition sheet comprising:
a sheet-shaped first flexible base material;
a plurality of first electrodes that are arranged on one surface of the first flexible base material and are contactable with the first living body part; and
at least one separator that is formed in the first flexible base material, is formed between prescribed ones of the first electrodes and includes one end arranged at an edge of the first flexible base material and another end arranged in a surface of the first flexible base material,
the reference potential acquisition sheet comprising a plurality of second electrodes that are arranged at a prescribed interval along an extending direction and are each attachable to the second living body part at which the reference potential is acquired, wherein the electrode sheet further comprises a film base material between the first flexible base material and the reference potential acquisition sheet, the film base material is configured to be directly attached to the first flexible base material and the reference potential acquisition sheet, and wherein the film base material has an in-plane stiffness higher than the first flexible base material.

2. The electrode sheet according to claim 1 wherein the separator comprises:
a linear part that extends from one end to another end; and
a hole part-that has a circular shape in a plan view and is provided consecutively to the linear part at a position of the other end.

3. The electrode sheet according to claim 2, wherein the linear part is arranged so as not to intersect with another linear part.

4. The electrode sheet according to claim 1, wherein the biological signal acquisition sheet further comprises a board that is overlaid on one surface of the first flexible base material and comprises a notch part with a part overlapping the first flexible base material being cut out.

5. The electrode sheet according to claim 4, wherein the board is divided into a plurality of areas and is peelable from the first flexible base material on an area-by-area basis.

6. The electrode sheet according to claim 4, wherein the notch part is arranged in the board in an area-by-area basis.

7. The electrode sheet according to claim 1, wherein the biological signal acquisition sheet further comprises a reinforcing sheet arranged to be overlaid on another surface of the first flexible base material along an edge of the other surface.

8. The electrode sheet according to claim 1, wherein the biological signal acquisition sheet comprises a plurality of separators formed in the first flexible base material, wherein each of the plurality of first electrodes arranged on the first flexible base material is separated from the other one of the plurality of first electrodes by each of the plurality of separators, and one end of each of the plurality of separators is positioned at an edge of the first flexible base material and the other end of each of the plurality of separators is positioned in the surface of the first flexible base material such that the first flexible base material is separated into multiple strips.

9. An electrode sheet for acquiring a biological signal, comprising:
a biological signal acquisition sheet configured to be attached to the living body part at which the biological signal is acquired; and
a reference potential acquisition sheet acquiring a reference potential,
the biological signal acquisition sheet comprising:
a sheet-shaped first flexible base material;
a plurality of first electrodes that are arranged on one surface of the first flexible base material and are contactable with the living body part; and
at least one separator formed in the first flexible base material, formed between prescribed ones of the first electrodes and includes one end arranged at an edge of the first flexible base material and another end arranged in a surface of the first flexible base material,
wherein the electrode sheet further comprises a film base material between the first flexible base material and the reference potential acquisition sheet, the film base material is configured to be directly attached to the first flexible base material and the reference potential acquisition sheet, and wherein the film base material has an in-plane stiffness higher than the first flexible base material.

10. The electrode sheet according to claim 9, wherein the separator comprises:
a linear part that extends from one end to another end; and
a hole part-that has a circular shape in a plan view and is provided consecutively to the linear part at a position of the other end.

11. The electrode sheet according to claim 10, wherein the linear part is arranged so as not to intersect with another linear part.

12. The electrode sheet according to claim 9, wherein the biological signal acquisition sheet further comprises a board that is overlaid on one surface of the first flexible base material and comprises a notch part with a part overlapping the first flexible base material being cut out.

13. The electrode sheet according to claim 12, wherein the board is divided into a plurality of areas and is peelable from the first flexible base material on an area-by-area basis.

14. The electrode sheet according to claim 12, wherein the notch part is arranged in the board in an area-by-area basis.

15. The electrode sheet according to claim 9, wherein the biological signal acquisition sheet further comprises a reinforcing sheet arranged to be overlaid on another surface of the first flexible base material along an edge of the other surface.

16. An electrode sheet for acquiring a biological signal, comprising:
a biological signal acquisition sheet configured to be attached to a first living body part at which the biological signal is acquired, wherein the biological signal acquisition sheet comprises a first flexible base material; and
a reference potential acquisition sheet that extends from the biological signal acquisition sheet and is configured to be attached to a second living body part at which a reference potential is acquired,
the reference potential acquisition sheet comprising a plurality of electrodes that are arranged at a prescribed interval along an extending direction of the reference potential acquisition sheet and are each attachable to the second living body part at which the reference potential is acquired,
wherein the electrode sheet further comprises a film base material between the first flexible base material and the reference potential acquisition sheet, the film base material is configured to be directly attached to the first flexible base material and the reference potential acquisition sheet, and wherein the film base material has an in-plane stiffness higher than the first flexible base material.

17. The electrode sheet according to claim 16, wherein the reference potential acquisition sheet further comprises:
a sheet-shaped second flexible base material; and
a second wiring line formed on the second flexible base material along the extending direction, and
the plurality of electrodes are each electrically connected to the second wiring line.

18. The electrode sheet according to claim 16, wherein the reference potential acquisition sheets comprises a plurality of reference potential acquisition sheets extending from the biological signal acquisition sheet.

19. The electrode sheet according to claim 18, wherein the reference potential acquisition sheet comprises a pair of the reference potential acquisition sheets provided on opposite sides of the biological signal acquisition sheet.

20. The electrode sheet according to claim 16, wherein the reference potential acquisition sheet is folded at a middle part in the extending direction.

\* \* \* \* \*

UNITED STATES PATENT AND TRADEMARK OFFICE
CERTIFICATE OF CORRECTION

Page 1 of 1

PATENT NO. : 12,121,356 B2
APPLICATION NO. : 17/052513
DATED : October 22, 2024
INVENTOR(S) : Tsuyoshi Sekitani et al.

It is certified that error appears in the above-identified patent and that said Letters Patent is hereby corrected as shown below:

In the Claims

In Column 13, Claim 2, Line no. 11, delete "to claim 1 wherein" and insert --to claim 1, wherein--.

Signed and Sealed this
Twenty-fifth Day of February, 2025

Coke Morgan Stewart
*Acting Director of the United States Patent and Trademark Office*